United States Patent [19]

O'Hanlon et al.

[11] 4,389,410

[45] Jun. 21, 1983

[54] ESTERS OF MONIC ACID A USEFUL AS ANTIBACTERIAL AND ANTIMYCOPLASMAL AGENTS

[75] Inventors: Peter J. O'Hanlon, Redhill; Norman H. Rogers, Horsham, both of England

[73] Assignee: Beecham Group Limited, England

[21] Appl. No.: 285,612

[22] Filed: Jul. 21, 1981

[30] Foreign Application Priority Data

Jul. 24, 1980 [GB] United Kingdom ................. 8024221

[51] Int. Cl.³ ..................... A61K 31/35; C07D 309/06
[52] U.S. Cl. .................................. 424/283; 542/426; 542/427; 549/414; 549/417
[58] Field of Search ................. 260/345.8 R; 542/427, 542/426; 424/283; 549/414, 417

[56] References Cited

U.S. PATENT DOCUMENTS 4,102,901 7/1978 Luk et al. ................... 260/345.8 R

*Primary Examiner*—Nicky Chan
*Attorney, Agent, or Firm*—Jacobs & Jacobs

[57] ABSTRACT

Compounds of formula (II):

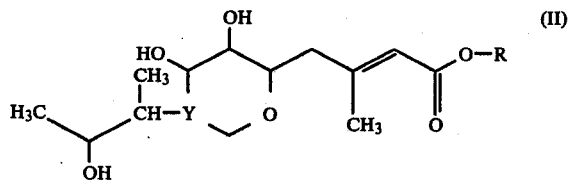

wherein
R is $C_{1-20}$ alkyl; $C_{3-8}$ cycloalkyl; $C_{3-20}$ alkenyl; aralkyl; cycloalkylalkyl; heterocyclyl or heterocyclylalkyl; each being substituted with formyl;

and Y is 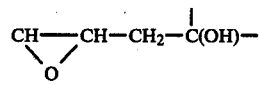

have activity against human and veterinary bacteria and mycoplasma. They may be produced by conventional methods and are used in conventional formulations.

10 Claims, No Drawings

ESTERS OF MONIC ACID A USEFUL AS ANTIBACTERIAL AND ANTIMYCOPLASMAL AGENTS

This invention relates to antibacterial compounds and in particular to a class of aldehydes which have antibacterial activity against certain Gram-positive and Gram-negative organisms, and also possess anti-mycoplasmal activity. The compounds are therefore of value in the treatment of human and veterinary infections.

The compounds of formula (I) and salts and esters thereof:

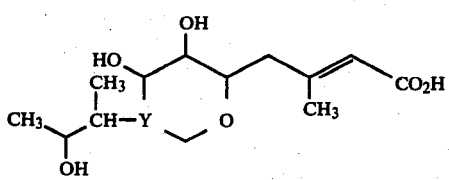 (I)

wherein Y represents

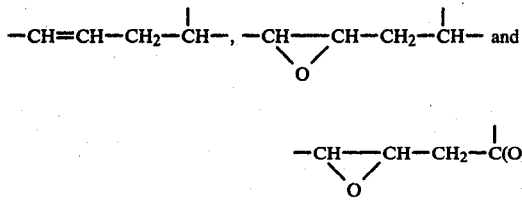

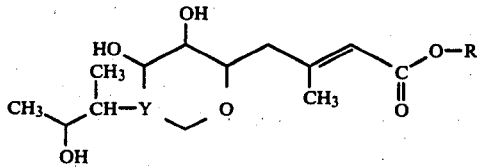

are disclosed in West German Offenlegungsschriften Nos. 2726619, 2726618 and 2848687 and European Patent Application No. 79300371.6. Compounds of formula (I) having the tri-substituted double bond in the E-configuration are referred to as monic and C, monic acid A and monic acid B respectively.

The present invention provides an aldehydic ester of formula (II):

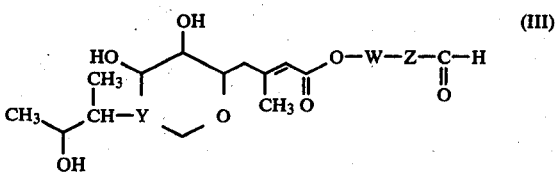 (II)

wherein Y is as defined with respect to formula (I); and R represents a $C_{1-20}$ alkyl, $C_{3-8}$ cycloalkyl, $C_{3-20}$ alkenyl, aralkyl, cycloalkylalkyl, heterocyclyl or heterocyclylalkyl group, which group is substituted with a formyl group. Preferably the compounds of formula (II) are derivatives of monic acid A, i.e. Y represents

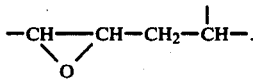

Suitably the group R represents $C_{3-10}$ alkyl substituted with a formyl group.

The compound (II) of this invention incorporates a tri-substituted double bond and may therefore exist in both the E (natural) and Z (or iso) geometrical forms. It is to be understood that both geometrical isomers of the compound of formula (II) are included within the scope of this invention, as well as mixtures of the two isomers. However, because in general the E-isomer of a particular derivative of compound (II) has the greater activity, it is preferable to employ that isomer.

In addition the 10, 11 double bond in the C-series of compounds is naturally E in configuration.

One sub-class of compounds of this invention comprises compounds of formula (III):

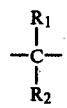 (III)

wherein Y is as defined with respect to formula (I); Z represents straight or branched chain $C_{1-11}$ alkylene group an aryl or monocyclic heteroaryl group or is absent; when W represents $$-\underset{R_2}{\overset{R_1}{\underset{|}{\overset{|}{C}}}}-$$

wherein $R_1$ and $R_2$ are each independently a hydrogen atom or a methyl group.

Preferably Z represents a straight chain $C_{1-11}$ alkylene group, or phenyl or monocyclic heteroaryl group especially furyl.

Compounds of this invention have antibacterial and antimycoplasmal activity, and are therefore of value in the treatment of bacterial and mycoplasma-induced human and veterinary diseases.

The infections against which compounds of this invention are particularly useful include venereal disease. They are also effective in the treatment of respiratory infections such as bacterial bronchitis; and bacterial meningitis, non-specific urethritis and pseumonia. In animals it may be employed for the treatment of mastitis in cattle, for swine dysentery, and for mycoplasma infections in animals such as turkeys, chickens, pigs and cattle.

Some of the human and veterinary diseases either caused by mycoplasma species or in which they play a prominent role, and against which compounds of this invention are effective, are as follows:

| Avian | |
|---|---|
| M gallisepticum | Chronic respiratory diseases (air-sacculitis) of chickens and turkeys |
| M synoviae | Airsacculitis and infections synovitis |
| Bovine | |
| M-bovis | Mastitis, respiratory disease and arthritis of cattle |
| M dispar | Calf pneumonia |
| Porcine | |
| M suipneumoniae | Enzootic pneumonia of pigs |
| M hyorhinis | } arthritis in pigs |
| M hyosynoviae | |
| Human | |
| M pneumoniae | primary atypical pneumonia |

Compounds of the present invention are particularly useful in the treatment of enzootic pneumonia in animals such as pigs, cattle and sheep, because they also have activity against the bacteria *Bordetella bronchispetica, Pasteurella multocida* and Haemophilus spp, which often cause respiratory complications in cases of this disease.

This invention also provides a pharmaceutical or veterinary composition which comprises a compound of formula (II) together with a pharmaceutically or veterinary acceptable carrier or excipient.

The compositions may be formulated for administration by any route, and would depend on the disease being treated. The compositions may be in the form of tablets, capsules, powders, granules, lozenges, liquid or gel preparations, such as oral, topical or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin compounds of this invention may be made up into a cream, lotion or ointment. Cream or ointment formulations that may be used for compounds of formula (II) are conventional formulations well known in the art, for example, as described in standard text books of pharmaceutics and cosmetics, such as Harry's Cosmeticology published by Leonard Hill Books, and the British Pharmacopoeia.

Suppositories will contain conventional suppository bases, eg cocoa-butters or other glyceride.

For parenteral administration, fluid unit dosage forms are prepared utilizing the compound and a sterile vehicle, water being preferred. The compound, depending on the vehicle and concentration used, can either be suspended or dissolved in the vehicle. In preparing solutions the compound can be dissolved in water for injection and filter sterilized before filling into a suitable vial or ampoule and sealing. Advantageously, adjuvants such as a local anaesthetic, preservative and buffering agents can be dissolved in the vehicle. To enhance the stability the composition can be frozen after filling into the vial and water removed under vacuum. The dry lypophilized powder is then sealed in the vial. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compounds.

Veterinary compositions for intrammary treatment of mammary disorders in animals, especially bovine mastitis, will generally contain a suspension of a compound of formula (II) in an oily vehicle.

The compositions may contain from 0.1% to 99% by weight, preferably from 10–60% by weight, of the active material, depending on the method of administration. Where the compositions comprise dosage units, each unit will preferably contain from 50–500 mg, of the active ingredient. The dosage as employed for adult human treatment will preferably range from 100 mg to 3 g, per day, for instance 250 mg to 2 g, per day, depending on the route and frequency of administration.

Alternatively a compound of formula (II) may be administered as part of the total dietary intake. In this case the amount of compound employed may be less than 1% by weight of the diet and in preferably no more than 0.5% by weight. The diet for animals may consist of normal foodstuffs to which the compound may be added or it may be added to a premix.

A suitable method of administration of a compound of formula (II) to animals is to add it to the animals' drinking water. In this case a concentration of compound in the drinking water of about 5–500 μg/ml, for example 5–200 μg/ml, is suitable.

Compounds of formula (II) may be prepared by reacting an aldehyde of formula (IV):

$$X-R-CHO \tag{IV}$$

in which X is a good leaving group, preferably a halogen atom or an alkyl or aryl sulphonate and R is as defined with respect to formula (II), with a salt of the acid of formula (I), preferably the sodium salt. A suitable halogen atom is chlorine, and a suitable sulphonate group is mesylate.

The reaction is preferably carried out in an organic solvent, suitably dimethylformamide, at 25° to 100° C. and the resulting product may be purified chromatographically on silica.

An alternative process for the preparation of compounds of formula (II) comprises reacting a monic acid mixed anhydride with a compound of formula ROMgX' or ROLi, in which R is defined with respect to formula (II) and X' is a good leaving group, preferably a halogen atom, such as chlorine. This process is only suitable for R radicals which do not contain acidic protons.

Compounds of formula (II) wherein Y represents

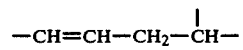

may also be prepared from compounds of formula (II) wherein Y represents

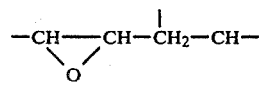

by reaction with a reagent which converts an epoxide to an olefin. Such reactions are described in our European Patent Applications Nos. 78300530.9 and 79300371.6.

Prior to the above processes of this invention, it may be desirable to protect the hydroxyl groups in compounds of formula (I). Although reaction is possible without hydroxyl protection, in some cases higher yields could be formed if the hydroxyl groups were protected. Such protecting groups must be removable under suitably mild conditions and suitable groups include silyl groups produced from a silylating agent as discussed above. Particularly suitable hydroxyl-protecting groups include tri-methylsilyl, t-butyldimethylsilyl, methylthiomethyl and β-methoxyethoxymethyl. A preferred hydroxyl-protecting group is trimethylsilyl, as it is readily removed on completion of the reaction. Alternatively, for some reactions it is possible to protect the hydroxyl groups with ester radicals which may be removed by chemical or enzymatic means. A particular example includes the formate group which may be removed under mild basic conditions such as aqueous sodium bicarbonate or by refluxing in aqueous methanol.

It is also possible to protect the glycol moiety in compounds of formula (I) and suitable reagents for forming such a hydroxyl-protecting group include compounds of formula (V):

wherein $R^3$ is hydrogen or a $C_{1-6}$ alkyl group and $R^4$, $R^5$ and $R^6$ independently represent a $C_{1-6}$ alkyl group.

The group $R^3$ may be for example hydrogen, methyl, ethyl, n- or iso-propyl. Most suitably, $R^3$ represents hydrogen so that the compound of formula (V) is a trialkyl orthoformate.

Groups $R^4$, $R^5$ and $R^6$ may be for example, methyl, ethyl, n- or iso-propyl, n- iso-, sec- or tert-butyl. Preferably $R^4$, $R^5$ and $R^6$ are all the same and each represents a methyl group.

Other glycol protecting groups include those wherein the glycol moiety is converted to the structure:

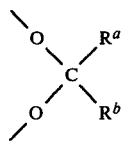

where $R^a$ and $R^b$ are hydrogen, $C_{1-6}$ alkyl, or phenyl. Preferably $R^a$ and $R^b$ are both methyl, i.e. the group is the isopropylidene group. This group may be introduced by reaction with 2,2-dimethoxypropane, and removed by treatment with acetic acid.

The hydroxy-protecting group may be removed by a conventional method for the particular hydroxyl-protecting group.

It may be such that it can be removed directly or, alternatively, it may be converted into a different protecting group which is then removable under different conditions. This latter approach may be employed when a glycol protecting group derived from a compound (V) is used; it is converted by acid to the group—$OCOR^1$ which is then removed.

The following Examples illustrate the present invention.

EXAMPLE 1 5-FORMYLPENTYL MONATE A

(i) 6-Chlorohexanal

To a suspension of pyridinium chlorochromate (11.8 g) in methylene chloride (75 ml) was added 6-chlorohexanol (5 g). The reaction was stirred at room temperature for 4 hours, then poured into ether (400 ml). After filtering through celite, the ether was evaporated to give the product (2.5 g, 51%), $\nu_{max}$ (film) 1721 cm$^{-1}$; $\delta_H$(CDCl$_3$) 1.3–2.0 (6H, m, (C$\underline{H}_2$)$_3$), 2.35 (2H, m, C$\underline{H}_2$CHO), 3.50 (2H, t, C$\underline{H}_2$Cl), 9.78 (1H, t, C$\underline{H}$O).

(ii) 5-Formylpentyl monate A

To a solution of sodium monate A (1.1 g) in DMF (50 ml) was added 6-chlorohexanal (0.444 g) and sodium iodide (0.450 g). The reaction was heated at 80° C. overnight then evaporated to an oil which was redissolved in ethyl acetate/brine and the organic layer washed with sodium bicarbonate and brine then dried (MgSO$_4$). The solvent was removed in vacuo and the residual oil chromatographed on on silica (15 g) eluting with 0–6% methanol-chloroform. Pure fractions (t.l.c.) were combined and evaporated to give (375 mg, 28%). H.p.l.c. indicated purity of 78% and product rechromatographed on silica (5 g) to give pure 5-formylpentyl monate A as an oil. (120 mg, 9%), $\nu_{max}$ (CHCl$_3$) 3400 (broad), 1725 and 1640 cm$^{-1}$; $\lambda_{max}$(EtOH) 221 nm ($\epsilon_m$ 13,458); $\delta_H$(CDCl$_3$) 0.88 (3H, d, C$\underline{H}_3$-17), 1.17 (3H, d, C$\underline{H}_3$-14), 2.15 (3H, s, C$\underline{H}_3$-15), 4.05 (2H, t, CO$_2$C$\underline{H}_2$), 5.75 (1H, s, H-2), 9.78 (1H, t, C$\underline{H}$O); $\delta_c$ (CDCl$_3$) 166.7 (C1), 156.7 (C3), 117.7 (C2), 75.0 (C5), 71.4 (C13), 71.4 (C13), 70.6 (C7), 69.2 (C6), 65.4 (C16), 63.4 (C6'), 61.2 (C11), 55.6 (C10), 43.7 (C2'), 42.9 (C4,12), 39.7 (C8), 31.7 (C9), 28.6 (C5', 25.7, 21.7 (C3',4'), 20.8 (C14), 19.2 (C15), 12.7 (C17); m/e (relative intensity) 442 (M+, 1%), 424 (1), 406 (1), 380 (1), 227 (98) (Found: 442.2549.C$_{23}$H$_{38}$O$_8$ requires 442.2532).

EXAMPLE 2

5-Formylfurfuryl monate A

A mixture of 5-hydroxymethylfurfuraldehyde (0.5 g, 4 mmol) and triphenylphosphine (1.3 g, 5 mmol) in dry carbon tetrachloride (3 ml) was heated at reflux for 30 min and then filtered to give an unstable 1 M solution of 5-chloromethylfurfuraldehyde.

A solution containing sodium monate A (1.1 g) in dimethylformamide (45 ml) was treated with the chloride (3 mM) and stirred overnight at room temperature. After evaporation to dryness, the residue was taken up in ethyl acetate/brine and the organic layer washed with aqueous sodium bicarbonate, brine, then dried (magnesium sulphate) and evaporated in vacuo. The resulting oil was chromatographed (silicagel, eluting with methanol in methylene chloride) to yield 5-formylfurfuryl monate A as a yellow oil (0.4 g, 30%).

ir spectrum: $\nu_{max}$ (film) 3450, 1720, 1680, 1650, 730 cm$^{-1}$.

U.V. spectrum: $\lambda_{max}$ (EtOH) 224 nm ($\epsilon_m$ 17,500), 276 nm ($\epsilon_m$ 17,000).

$^1$Hnmr: δH (CDCl$_3$) 9.74 (1H, s, CHO), 7.22 (1H, s, H4''), 6.60 (1H, s, H3''), 5.79 (1H, s, H2), 5.14 (2H, s, H1'), 2.20 (3H, s, CH$_3$-15), 1.20 (3H, d, CH$_3$-15), 1.20 (3H, d, CH$_3$-14), 0.90 (3H, d, CH$_3$-17).

$^{13}$Cnmr: $\delta_C$ (CDCl$_3$) 177.8 (CHO), 165.6 (C1), 159.2 (C3), 156.3 (C5″), 152.9 (C2″), 121.7 (C4″), 116.4 (C2), 112.3 (C3″), 75.0 (C5), 71.2 (C13), 70.4 (C7), 69.0 (C6), 65.4 (C16), 61.2 (C11), 5 7.1 (C1′), 55.6 (C10), 43.0 (C12), 42.8 (C4), 39.6 (C8), 31.7 (C9), 20.8 (C14), 19.4 (C15), 12.6 (C17).

mass spectrum: m/e (relative intensity) 452 (M$^+$, 1%), 3 25 (6), 227 (18), 109 (100) (Found: 452.2035. C$_{23}$H$_{32}$O$_9$ requires 452.2044).

EXAMPLE 3 p-Formylbenzyl monate A

Thionyl chloride (15 ml, 200 mmol) was added dropwise to p-toluic acid (13.7 g, 100 mmol) in ether (80 ml) and heated under reflux for 7 h. Further thionyl chloride (10 ml, 130 mmol) was added and reaction refluxed for 16 h, then evaporated in vacuo. N-Bromosuccinimide (17.8 g, 100 mmol), benzoyl peroxide (100 mg) and carbon tetrachloride (45 ml) were added and the reaction refluxed for 4 h, cooled, filtered and the filtrate evaporated in vacuo. Further N-bromosuccinimide (8.9 g, 50 mmol), benzoyl peroxide (60 mg) and carbon tetrachloride were added to the residue and the reaction refluxed for 2 h. The reaction was cooled, filtered, the residue washed with carbon tetrachloride and the combined filtrates evaporated in vacuo. The residue was crystallized from petroleum ether (fraction boiling at 40°-60° C.) to yield 4-bromomethyltoluoyl chloride. (14.8 g, 64%), m.p. 165°-170° C.

$^1$Hnmr: $\delta_H$ (CDCl$_3$) 8.35-7.25 (4H, ABq, aryl), 4.55 (2H, s, C$\underline{H}_2$).

A solution of the 4-bromomethyltoluoyl chloride (3.48 g. 15 mmol) in dry tetrahydrofuran (15 ml) was added dropwise to a solution of lithium tri-t-butoxyaluminium hydride (3.81 g, 15 mmol) in dry tetrahydrofuran (50 ml) at −70° C., stirred for 2 h, allowed to warm to room temperature and stirred for a further 1 h. The reaction was poured into water, filtered, extracted with ethyl acetate, dried (magnesium sulphate), and evaporated in vacuo to yield 4-bromomethylbenzaldehyde (1.31 g, 44%).

$^1$Hnmr: $\delta_H$(CDCl$_3$) 9.95 (1H, s, C$\underline{H}$O), 8.30-7.10 (4H, m, aryl), 4.45 (2H, s, CH$_2$). Sodium monate A (1.1 g, 3 mmol), 4-bromomethylbenzaldehyde (0.8 g, 4 mmol), and dimethyl formamide (30 ml) were stirred at 20° C. for 17 h and evaporated in vacuo. The residue was taken up in ethyl acetate, washed with aqueous sodium bicarbonate, then brine, dried (magnesium sulphate) and evaporated in vacuo. The resulting residue was purified by chromatography (15 g silicagel, 0 to 4% v/v methanol in dichloromethane) to yield p-formylbenzyl monate A as a colourless oil (331 mg, 24%).

ir spectrum: $\nu_{max}$ (film) 3440, 1710, 1640, 1610, 1580 cm$^{-1}$.

U.V. spectrum: $\lambda_{max}$ (EtOH) 211.5 nm ($\epsilon_m$ 19,326), 249 nm ($\epsilon_m$ 19,362).

$^1$Hnmr: $\delta_H$(CDCl$_3$) 10.01 (1H, s, C$\underline{H}$O), 7.89 and 7.52 (4H, ABq, aryl), 5.85 (1H, s, H2), 5.21 (2H, s, CH$_2$), 2.22 (3H, s, CH$_3$-15), 1.21 (3H, d, CH$_3$-14), 0.92 (3H, d, CH$_3$-17).

$^{13}$Cnmr: $\delta_C$ (CDCl$_3$) 192.0 (C7″), 166.1 (C1), 158.7 (C3), 143.5 (C4″), 136.0 (C1″), 129.9, 128.2 (C2″, 3″, 5″, 6″), 116.7 (C2), 75.0 (C5), 71.1 (C13), 70.4 (C7), 69.0 (C6), 65.5 (C16), 64.6 (C1′) 61.1 (C11), 55.6 (C10), 43.0 (C4), 42.8 (C12), 39.7 (C8), 31.7 (C9), 20.8 (C14), 19.3 (C15), 12.6 (C17).

mass spectrum: m/e (relative intensity) 462 (M$^+$, 0.24%), 325 (10), 227 (59), 119 (100) (Found: M$^+$, 462.2228. C$_{25}$H$_{34}$O$_8$ requires 462.2254).

EXAMPLE 4 m-Formylbenzyl monate A m-Toluic acid (13.6 g, 100 mmol) was taken up in methanol (95 ml) and concentrated sulphuric acid (5 ml) and refluxed for 3½ h. The reaction mixture was then evaporated to half volume, poured into water (50 ml), extracted with ethyl acetate, dried (magnesium sulphate), and evaporated in vacuo. N-Bromosuccinimide (17.8 g, 100 mmol), benzoyl peroxide (100 mg) and carbon tetrachloride (100 ml) were added and refluxed for 2½ H. The reaction mixture was filtered and the residue washed with carbon tetrachloride. The filtrates were combined and evaporated in vacuo giving 3-bromomethyl benzoate (20.6 g, 90%).

$^1$Hnmr: $\delta_H$(CDCl$_3$) 8.30-7.20 (4H, m, aryl), 4.45 (2H, s, C$\underline{H}_2$), 3.85 (3H, s, C$\underline{H}_3$).

A solution of diisobutyl aluminium hydride in toluene (30 ml, 25% w/v, 40 mmol) was added dropwise to a solution of 3-bromomethyl benzoate (4.6 g, 20 mmol) in toluene (50 ml) at −30° C. The reaction was stirred for 1½ h, allowed to warm to room temperature and quenched with methanol. The reaction mixture was filtered, extracted with ethyl acetate, washed with aqueous sodium bicarbonate solution, then brine, dried (magnesium sulphate), and evaporated in vacuo giving 3-bromomethylbenzyl alcohol (2.28 g, 56%).

$^1$Hnmr: $\delta_H$(CDCl$_3$) 7.6-7.0 (4H, m, aryl), 4.55 (2H, s, CH$_2$), 4.45 (2H, s, C$\underline{H}_2$Br).

3-Bromomethylbenzyl alcohol (1.015 g, 5 mmol) and activated manganese (IV) oxide (10 g) in acetone (30 ml) were stirred at 20° C. for 22 h. The reaction mixture was filtered and the filtrate evaporated in vacuo to yield 3-bromomethylbenzaldehyde as a pale yellow liquid (547 mg, 55%).

$^1$Hnmr: $\delta_H$(CDCl$_3$) 9.95 (1H, s, C$\underline{H}$O), 8.20-7.15 (4H, m, aryl), 4.50 (2H, s, C$\underline{H}_2$).

3-Bromomethylbenzaldehyde (547 mg, 2.8 mmol), sodium monate A (1.1 g, 3 mmol), and dimethylformamide (25 ml) were stirred at 20° C. for 18 h and then evaporated in vacuo. The residue was taken up in ethyl acetate, washed with aqueous sodium bicarbonate and then brine, dried (magnesium sulphate), and evaporated in vacuo. The residual yellow oil was purified by chromatography (15 g silicagel, 0 to 4% v/v methanol in dichloromethane). Pure fractions were combined to yield m-formylbenzyl monate A as a colourless oil (654 mg, 51%).

ir spectrum: $\nu_{max}$ (film) 3440, 1710, 1640, 1610, 1590 cm$^{-1}$.

U.V. spectrum: $\nu_{max}$ (EtOH) 224 nm ($\epsilon_m$ 19,012).

$^1$Hnmr: $\delta_H$ (CDCl$_3$) 10.10 (1H, s, C$\underline{H}$O), 8.10-7.25 (4H, m, aryl), 5.85 (1H, s, H2), 5.20 (2H, s, CH$_2$), 2.22 (3H, s, CH$_3$-15), 1.21 (3H, d, CH$_3$-14), 0.92 (3H, d, CH$_3$-17).

BIOLOGICAL DATA

(a) Anti-Mycoplasmal Activity

Table 1 shows the in vitro MIC values (μg/ml) of the compounds of the Examples against a number of mycoplasma organisms. The values were determined in Friis broth solidified with 0.9% agarose. The inoculum was 10$^3$ to 10$^5$ C.F.U. and the MIC's were recorded after 6 days incubation at 37° C.

TABLE 1

(a) Compound of Example 1

| ORGANISM | M.I.C. (μg/ml) |
|---|---|
| M. suipneumoniae NB12 | 0.5 |
| M. suipneumoniae JF 435 | 1.0 |
| M. suipneumoniae HK(2) | 1.0 |
| M. suipneumoniae Str. 11 | 0.5 |
| M. suipneumoniae J2206/183b | 1.0 |
| M. suipneumoniae MS 16 | 0.5 |
| M. suipneumoniae PW/C/210 | 0.5 |
| M. suipneumoniae LABER | 0.5 |
| M. suipneumoniae UCD 1 | 1.0 |
| M. suipneumoniae TAM 6N | 1.0 |
| M. suipneumoniae ATCC 25095 | 0.5 |
| M. suipneumoniae NCTC 10110 | 1.0 |
| M. hyorhinis ATCC 23234 | 0.25 |
| M. hyorhinis ATCC 25021 | 0.25 |
| M. hyosynoviae ATCC 25591 | 0.25 |
| M. bovis NCTC 10131 | <0.01 |
| M. bovigenitalium ATCC 14173 | 0.05 |
| M. dispar NCTC 10125 | 0.25 |
| M. gallisepticum S6 | 10 |
| M. pneumoniae ATCC 15492 | 1.0 |

TABLE 1(b)

(b) Compounds of Example 2

| ORGANISM | M.I.C.* (μg/ml) |
|---|---|
| M. suipneumoniae NB12 | 0.5 |
| M. suipneumoniae JF 435 | 0.5 |
| M. suipneumoniae HK(2) | 0.25 |
| M. suipneumoniae Str. 11 | 0.25 |
| M. suipneumoniae J2206/183b | 0.5 |
| M. suipneumoniae MS16 | 0.25 |
| M. suipneumoniae PW/C/210 | 0.25 |
| M. suipneumoniae LABER | 0.25 |
| M. suipneumoniae UCD 1 | 0.5 |
| M. suipneumoniae TAM 6N | 1.0 |
| M. suipneumoniae ATCC 25095 | 0.5 |
| M. suipneumoniae NCTC 10110 | 0.5 |
| M. hyorhinis ATCC 23234 | 0.5 |
| M. hyorhinis ATCC 25021 | 0.25 |
| M. hyosynoviae ATCC 25591 | 0.25 |
| M. bovis NCTC 10131 | 0.025 |
| M. bovigenitalium ATCC 14173 | 0.05 |
| M. dispar NCTC 10125 | 0.25 |
| M. gallisepticum S6 | 5.0 |
| M. pneumoniae ATCC 15492 | 5.0 |

TABLE 1(c)

(c) Compound of Example 3

| ORGANISM | M.I.C.* (μg/ml) |
|---|---|
| M. suipneumoniae NB12 | 0.25 |
| M. suipneumoniae JF 435 | 0.25 |
| M. suipneumoniae HK(2) | 0.25 |
| M. suipneumoniae Str. 11 | 0.25 |
| M. suipneumoniae J2206/183b | 0.25 |
| M. suipneumoniae MS16 | 0.1 |
| M. suipneumoniae PW/C/210 | 0.1 |
| M. suipneumoniae LABER | 0.1 |
| M. suipneumoniae UCD 1 | 0.25 |
| M. suipneumoniae TAM 6N | 0.5 |
| M. suipneumoniae ATCC 25095 | 0.25 |
| M. suipneumoniae NCTC 10110 | 0.25 |
| M. hyorhinis ATCC 23234 | 0.1 |
| M. hyorhinis ATCC 25021 | 0.1 |
| M. hyosynoviae ATCC 25591 | 0.05 |
| M. bovis NCTC 10131 | <0.01 |
| M. bovigenitalium ATCC 14173 | NG |
| M. dispar NCTC 10125 | 0.05 |
| M. gallisepticum S6 | 1.0 |
| M. pneumoniae ATCC 15492 | 0.5 |

(b) VETERINARY BACTERIA

Table 2 shows the MIC values (μg/ml) of the compounds of the Examples against a number of organisms important in veterinary infections. The values were determined using a two fold serial dilutions in Diagnostic Sensitivity Test Agar with the inoculum of $10^4$ organisms and incubation for 18 hours at 37° C.

TABLE 2

(a) Compound of Example 1

| ORGANISM | AGAR |
|---|---|
| E. coli NCTC 10418 | >80 |
| E. coli E1 | >80 |
| S. dublin S7 | >80 |
| S. typhimurium S18 | >80 |
| Bord. bronchiseptica B08 | 5 |
| Bord. bronchiseptica B09 | 1.25 |
| Past. multocida PA1 | 1.25 |
| Past. multocida PA2 | .625 |
| Past. haemolytica PA5 | 20 |
| Erysipelothrix rhusiopathiae NCTC 8163 | 80 |
| Corynebacterium pyogenes CY1 | >80 |
| Staph. aureus B4 (pen. resistant) | .156 |
| Staph. aureus 152 (pen. sens.) | .156 |
| Staph. aureus Oxford | .156 |
| Strep. suis (group D) SPS11 | 20 |
| Strep. uberis SPU1 | .312 |
| Strep. dysgalaciae SPD1 | .039 |
| Strep. agalactiae SPA1 | 1.25 |
| B. subtilis ATCC 6633 | NG |

TABLE 2(b)

(b) Compound of Example 2

| ORGANISM | AGAR |
|---|---|
| E. coli NCTC 10418 | >80 |
| E. coli E1 | >80 |
| S. dublin S7 | >80 |
| S. typhimurium S18 | >80 |
| Bord. bronchiseptica B08 | >80 |
| Bord. bronchiseptica B09 | 10 |
| Past. multocida PA1 | 2.5 |
| Past. multocida PA2 | 2.5 |
| Past. haemolytica PA5 | 20 |
| Erysipelothrix rhusiopathiae NCTC 8163 | >80 |
| Corynebacterium pyogenes CY1 | >80 |
| Staph. aureus B4 (pen. resistant) | 2.5 |
| Staph. aureus 152 (pen. sens.) | 2.5 |
| Staph. aureus Oxford | 2.5 |
| Strep. suis (group D) SPS11 | 40 |
| Strep. uberis SPU1 | 0.625 |
| Strep. dysgalactiae SPD1 | 1.25 |
| Strep. agalactiae SPA1 | 2.5 |
| B. subtilis ATCC 6633 | NG |

NG - no growth

(c) HUMAN BACTERIA

Table 3 shows the MIC values (μg/ml) of the compounds of the Examples against a number of organisms important in human infections. The values were determined by serial dilutions in nutrient agar with 5% chocolated horse blood after incubations for 18 hours at 37° C.

TABLE 3

(a) Compounds of Example 1

| ORGANISM | M.I.C. (μg./ml.) AGAR |
|---|---|
| E. coli NCTC 10418 | >100 |
| E. coli ESS | 2.5 |
| P. mirabilis 889 | 100 |
| K. aerogenes A | >100 |
| Ps. aeruginosa NCTC 10662 | >100 |
| Pasteurella multacida 1633 | 1.0 |
| Haemophilus influenzae Q1 | — |
| Haemophilus influenzae Wy21 | 0.5 |
| Neisseria catarrhalis 1502 | >0.02 |
| Bacillus subtilis 6633 | 0.5 |
| Corynebacterium xerosis 9755 | >100 |

TABLE 3-continued

(a) Compounds of Example 1

| ORGANISM | M.I.C. (μg./ml.) AGAR |
|---|---|
| Sarcina lutea 8340 | >100 |
| Staph. aureus Oxford | 0.05 |
| Staph. aureus Russell | 0.2 |
| Staph. aureus W2827 | 0.1 |
| Strep. faecalis I | >100 |
| Strep. pyogenes A 64/848 | 0.5 |
| Strep. pyogenes B 2788 | 1.0 |
| Strep. pyogenes C 2761 | 1.0 |
| Strep. pneumoniae 1760 | — |

TABLE 3(b)

(b) Compound of Example 2

| ORGANISM | M.I.C. (μg/ml) AGAR | BROTH |
|---|---|---|
| E. Coli NCTC 10418 | >100 | $10^{-2}$ 50 |
| E. coli ESS | 10 | |
| P. mirabilis 889 | 100 | |
| K. aerogenes A | >100 | |
| Ps. aeruginosa 10662 | >100 | |
| Pasteurella multocida 1633 | 1.0 | |
| Haemophilus influenzae Q1 | — | |
| Haemophilus influenzae Wy21 | 0.5 | |
| Neisseria catarrhalis 1502 | 0.25 | |
| Bacillus subtilis 6633 | 1.0 | |
| Corynebacterium xerosis 9755 | >100 | |
| Sarcina lutea 8340 | >100 | |
| Staph. aureus Oxford | 0.25 | 0.25 |
| Staph. aureus Russell | 1.0 | 0.5 |
| Staph. aureus W2877 | 0.5 | |
| Strep. faecalis I | >100 | |
| Strep. pyogenes R80/421-A | 1.0 | |
| Strep. agalactiae 2788-B | 2.5 | |
| Strep. spp. 64/848-C | 2.5 | |
| Strep. pneumoniae CN33 | 2.5 | |

We claim:

1. A compound of formula (II):

wherein
Y is selected from $-CH=CH-CH_2-CH-$; $-CH-CH-CH_2-CH-$ and
 $\phantom{-CH=CH-CH_2-CH-; -CH}\diagdown O \diagup$ $-CH-CH-CH_2-C-$;
 $\phantom{-}\diagdown O \diagup \phantom{-CH_2-}\overset{|}{OH}$ and
R is a group selected from $C_{1-20}$ alkyl, $C_{3-8}$ cycloalkyl; $C_{3-20}$ alkenyl; benzyl; cycloalkylalkyl; furyl and furyl alkyl; said group being substituted by formyl.

2. A compound according to claim 1 wherein R is formyl substituted benzyl or furfuryl.

3. A compound according to claim 1 and selected from 5-formylpentyl monate A; 5-formylfurfuryl monoate A; p-formylbenzyl monate A and m-formylbenzylmonate A.

4. The compound according to claim 1, wherein R is formylalkyl having 3 to 10 carbon atoms in the alkyl moiety.

5. A compound of formula (II):

wherein
Y is selected from $-CH=CH-CH_2-CH-$; $-CH-CH-CH_2-CH-$ and
 $\phantom{-CH=CH-CH_2-CH-; -CH}\diagdown O \diagup$ $-CH-CH-CH_2-C-$;
 $\phantom{-}\diagdown O \diagup \phantom{-CH_2-}\overset{|}{OH}$ wherein
R is $$-W-Z-\overset{O}{\underset{\|}{C}}-H, \text{ in which W is } -\overset{R_1}{\underset{R_2}{\overset{|}{\underset{|}{C}}}}-, R_1$$

and $R_2$ are each independently hydrogen or methyl and Z is straight or branched chain alkylene of 1 to 11 carbon atoms, phenyl, furyl or a direct bond.

6. The compound according to claim 5, wherein Z is straight chain alkylene of 1 to 11 carbon atoms, phenyl or furyl.

7. A compound according to claim 5 wherein R is selected from 5-formylpentyl; m-formylbenzyl; p-formylbenzyl and 5-formylfurfuryl.

8. A compound according to claim 5 wherein Y is $-CH-CH-CH_2-CH-$
 $\diagdown O \diagup$ 9. An antibacterial or antimycoplasmal, pharmaceutical or veterinary composition comprising an effective, non-toxic amount of a compound according to claim 1 and a pharmaceutically or veterinarily acceptable carrier therefor.

10. A method for treating humans or animals which method comprises administering an antibacterially or antimycoplasmally effective non-toxic amount of a compound according to claim 1 to a human or animal suffering from a bacterial or mycoplasmal infection.

* * * * *